United States Patent [19]
Pavanelli

[11] Patent Number: 6,132,445
[45] Date of Patent: Oct. 17, 2000

[54] DEVICE FOR THE CLEANING AND HYGIENE OF THE ORAL CAVITY, IN PARTICULAR OF THE TONGUE

[76] Inventor: Gianni Pavanelli, Via Portazza, 4, 40100 Bologna, Italy

[21] Appl. No.: 09/404,130

[22] Filed: Sep. 23, 1999

[51] Int. Cl.[7] .............. A61B 17/24; A61B 9/00
[52] U.S. Cl. ............................................. 606/161
[58] Field of Search .................. 606/161; 401/155; 433/89, 85; 601/137; 15/188; 604/277, 279

[56] References Cited

U.S. PATENT DOCUMENTS

| | | | |
|---|---|---|---|
| 2,218,072 | 10/1940 | Runnels ................................ | 15/188 |
| 5,098,291 | 3/1992 | Curtis et al. ........................... | 433/89 |
| 5,344,317 | 9/1994 | Pacher et al. ......................... | 433/85 |
| 5,382,106 | 1/1995 | Voigt ..................................... | 401/155 |
| 5,779,654 | 7/1998 | Foley et al. ........................... | 601/137 |

*Primary Examiner*—Michael Buiz
*Assistant Examiner*—Anthony S. King
*Attorney, Agent, or Firm*—William J. Sapone, Esq.; Nims, Howes, Collison, Hansen & Lackert

[57] ABSTRACT

A device for cleaning and improving the hygiene of the oral cavity and in particular of the tongue, comprises a rod 1 having a flat head 2 fixed to one end thereof. The head has two opposite flat surfaces 2a, each surface having a plurality of protuberances 3 thereon designed for scraping and brushing the upper tongue surface during cleaning. A fluid tank 8 can be located inside the rod 1, the fluid flowing through a channel 5 toward exit holes 6 made on the surfaces 2a of the head 2, or a cartridge can be attached at an end of the channel outside the rod. In each instance, fluid such as mouthwash is applied during cleaning.

8 Claims, 1 Drawing Sheet

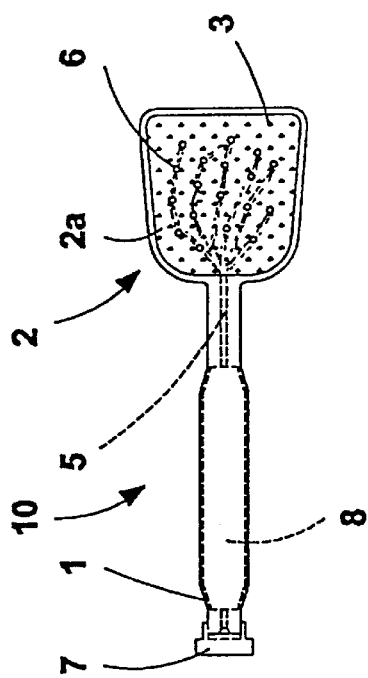
Fig. 3
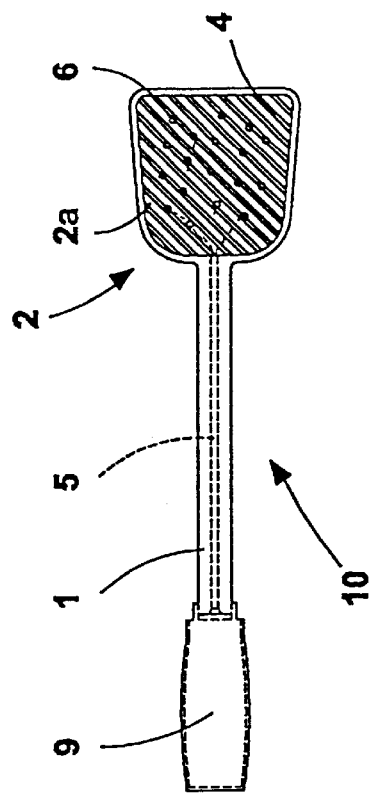
Fig. 4
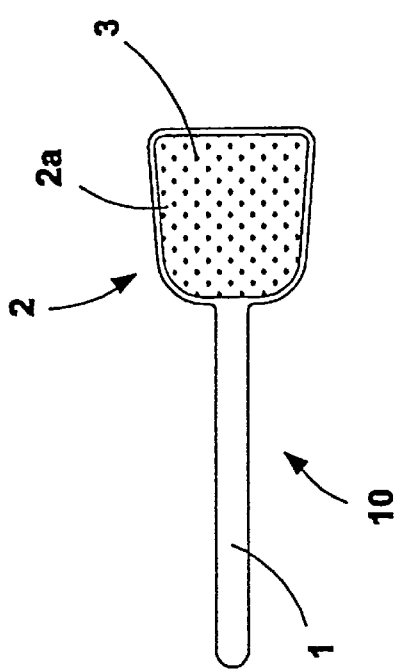
Fig. 1
Fig. 2

DEVICE FOR THE CLEANING AND HYGIENE OF THE ORAL CAVITY, IN PARTICULAR OF THE TONGUE

TECHNICAL FIELD

The present invention concerns devices for improving the hygiene of the oral cavity, in particular this invention refers to a device for cleaning the tongue.

BACKGROUND

It is known that the cleaning of the oral cavity is an important operation which should be frequently used to protect and defend the oral cavity from the attack of acids and bacterial agents generally. As known, in fact, these latter can lead to acute or chronic infections or degenerative phenomena, such as for example, caries and tartar, which damage the functionality as well as the aesthetics of the oral cavity internal surfaces, further causing other not very pleasant phenomena, as for example, halitosis.

In general, the oral cavity is cleaned by using a small toothbrush together with detergent, water, liquid or solutions, for example, toothpaste and mouthwash.

However, the complete cleaning of the oral cavity often cannot be obtained as not all surfaces can be reached, or can be reached only partially, because the users pay much attention to cleaning the teeth and so ignore almost totally the cleaning of the other internal surfaces of the oral cavity and in particular of the tongue.

Sometimes, the cleaning of this important organ is made by using the same toothbrush which is used for the teeth, or, in some African Countries it is tradition to brush the tongue with a wooden stick.

The disadvantage of using the toothbrushes or sticks for cleaning the tongue are that they are not made to meet the specific object, as toothbrushes have bristles having physical characteristics, for example the length, the hardness and the flexibility, which are suitable for an optimal cleaning of hard surfaces such as the teeth but not for soft surfaces such as the tongue. On the other hand, the irregular surface of the stick is so rough that does not allow a smooth tongue cleaning.

SUMMARY OF THE INVENTION

The main object of the present invention is to propose a device for the cleaning and the hygiene of the oral cavity, and in particular of the tongue, which is able to allow a regular, smooth and hence optimal cleaning of the tongue which allows a major prevention and protection against the attacks of the bacterial agents and/or pathogen inside the oral cavity.

A further object of the present invention is to propose a device with safe and reliable function and of simple use.

The above mentioned objects are obtained according to the present invention.

BRIEF DESCRIPTION OF THE DRAWINGS

The features of the present invention are described below with reference to the attached drawings, in which:

FIG. 1 shows a top view of the device of the present invention;

FIG. 2 shows a top view of a second embodiment of the device of FIG. 1;

FIG. 3 shows a top view of a third embodiment of the device of FIG. 1;

FIG. 4 shows a top view of the fourth embodiment of the device of FIG. 1.

DETAILED DESCRIPTION OF THE INVENTION

Referring to FIG. 1, a device 10 according to the invention includes a rod 1 having a head 2 fixed thereto in correspondence to one end thereof.

The head 2 is preferably constituted of semi-stiff material such as rubber, caoutchouc or silicon elastomer.

The head 2 defines two opposite flat surfaces, only one of them being visible in FIGS. 1 to 4, each surface having a plurality of protuberances 3, which in a preferred embodiment have a rounded shape, preferably being cylindrical, a truncated cone or spherical, the protuberances being distributed uniformly in an equidistant manner on each of said surfaces 2a.

The methods of using the device 10 are extremely simple since the user, holding the rod 1, can scrape the head 2 of the device on the tongue in such a way that the head surface 2a, because of its roughness due to the presence of the protuberances 3, allows the brushing and then a complete cleaning.

For this purpose it is possible to use the device 10 together with detergent and mouth-rinse liquids and solutions, for example, water, toothpaste and mouthwash.

In a second embodiment of the device 10 shown in FIG. 2, the protuberances 3 include a plurality of ribs 4 that are equally distributed and have a V-shape, for example, turned toward the rod 1. Furthermore, the head 2 is removably fixed to the rod 1, using a connection means 11, which can be, for example, being a snap clip or threaded attachment, so allowing the removal of the head 2 and its eventual substitution with another head 2 or with other tools fit for personal hygiene, for example, a toothbrush, a cylinder brush or a dental floss carrier, which are known and not shown here.

In a third embodiment shown in FIG. 3, the device 10 has a rod 1 with a channel 5 crossing inside. One channel end, being outside the rod 1, is closed by means of a plug 7, while the other end conducts fluid flow, by using the branches of the channel 5, with a plurality of exit holes 6 located on at least one surface 2a of the head 2.

Between the ends of the channel 5, there is an associated tank 8, which is totally or partially inserted into the rod 1. This tank 8 can contain a detergent or mouthwash liquid which flows toward the holes 6, due to gravity or by a pumping arising from user pressure on the lateral surfaces of the tank itself. The liquid comes out from the holes 6 during the tongue cleaning as the user moves the surfaces 2a of the device 10 on the upper surface of the tongue, preferably in a unidirectional way from the internal toward the external end of the oral cavity.

It is evident that, in such a case, the rod 1 is made of semi-stiff material suitable to allow compression of the tank 8 contained therein, or the tank 8 has at least a lateral surface positioned outside the rod 1.

A fourth embodiment shown in FIG. 4 has a device 10 similar to that of the third embodiment (FIG. 3) with the only difference being that the tank 8 is substituted by a cartridge 9 located outside the rod 1.

This cartridge 9 is attached, preferably being threaded or snapped onto the external end of the channel 5, the cartridge containing a detergent or mouthwash liquid which flows toward the holes 6 and comes out therefrom, either due to gravity or under pressure exerted manually by the user on the cartridge 9.

Advantageously, the particular configurations of the surfaces 2a of the head 2 can be interchanged in the fourth embodiment as above mentioned. Furthermore the protuberances 3 can be equally spaced and distributed on the surfaces 2a as well as being mainly grouped at the center thereof.

The main advantage of the present invention is that it provides a device for the cleaning and hygiene of the oral cavity, and in particular of the tongue, with an optimal cleaning to avoid the attack of bacterial agents generally on the tongue or in the oral cavity.

A further advantage of the present invention is that the device is safe, reliable and simple to use.

While preferred embodiments have been shown and described, it will be understood by those skilled in the art that various changes or modifications can be made without varying from the scope of the invention.

I claim:

1. A device for cleaning an oral cavity and a tongue, comprising:

a rod having a flat head fixed to an end thereof, said head having at least one flat surface having a plurality of protuberances for scraping and cleaning said tongue, said rod having a channel, the channel having a first end closed with a plug and a second end in fluid communication with a plurality of holes located on at least one surface of said head, a tank connected to said channel between said two ends and fit to contain a fluid which flows toward said holes through said channel to exit therefrom during cleaning.

2. The device according to claim 1 wherein said head 2 is removably fixed to said rod 1.

3. The device according to claim 2 wherein said head 2 is removed and a second head is fitted in its place.

4. The device according to claim 3 wherein the second head is selected from the group consisting of a toothbrush, a cylindrical brush or a dental floss carrier.

5. The device according to claim 1 wherein said protuberances 3 have a rounded shape.

6. The device according to claim 1 wherein said protuberances 3 consist of a plurality of ribs 4 spread into a V-shaped pattern.

7. The device according to claim 1 wherein said head 2 is made of semi-stiff material selected from the group consisting of rubber, caoutchouc or silicon elastomer.

8. The device according to claim 1 wherein said rod 1 has a channel 5, the channel having a first end and a second end in fluid communication with a plurality of holes 6 located on at least one surface 2a of said head 2, a cartridge 9 connected to the first end of said channel 5 and fit to contain a fluid which flows toward said holes 6 through said channel 5 to exit therefrom during cleaning.

* * * * *